US008992438B2

(12) United States Patent
Loktionov et al.

(10) Patent No.: US 8,992,438 B2
(45) Date of Patent: Mar. 31, 2015

(54) COLORECTAL CELL SAMPLING DEVICE

(75) Inventors: Alexandre Loktionov, Cambridge (GB); Andrew Humphrey Llewelyn, Lyme Regis (GB); Rupert Charles Gifford Lywood, Kidderminster (GB); Tatiana Bandaletova, Cambridge (GB); Colin George Ferrett, Oxford (GB); Hugo Geoffrey Gifford Lywood, Worcs (GB)

(73) Assignee: Colonix Limited, London (GB)

( * ) Notice: Subject to any disclaimer, the term of this patent is extended or adjusted under 35 U.S.C. 154(b) by 582 days.

(21) Appl. No.: 11/571,693

(22) PCT Filed: Jul. 6, 2005

(86) PCT No.: PCT/GB2005/002641
§ 371 (c)(1),
(2), (4) Date: Nov. 21, 2007

(87) PCT Pub. No.: WO2006/003447
PCT Pub. Date: Jan. 12, 2006

(65) Prior Publication Data
US 2008/0097238 A1 Apr. 24, 2008

(30) Foreign Application Priority Data
Jul. 7, 2004 (GB) .................................. 0415277.3

(51) Int. Cl.
*A61B 10/02* (2006.01)
*A61B 10/04* (2006.01)
*A61B 10/00* (2006.01)
A61B 17/00 (2006.01)
A61B 17/29 (2006.01)

(52) U.S. Cl.
CPC ............. *A61B 10/04* (2013.01); *A61B 10/0038* (2013.01); *A61B 10/0096* (2013.01); *A61B 2017/00557* (2013.01); *A61B 2017/2925* (2013.01)
USPC ......................................... 600/562; 600/572

(58) Field of Classification Search
USPC .................................................. 600/562, 572
See application file for complete search history.

(56) References Cited

U.S. PATENT DOCUMENTS

| 3,664,328 A | * | 5/1972 | Moyle et al. ................... 600/569 |
| 3,800,781 A | * | 4/1974 | Zalucki ......................... 600/562 |
| 4,467,816 A | * | 8/1984 | Schluter et al. ............... 600/569 |

(Continued)

FOREIGN PATENT DOCUMENTS

| WO | 8500100 A1 | 1/1985 |
| WO | 9423787 A | 10/1994 |
| WO | 0130243 A1 | 5/2001 |

*Primary Examiner* — Linda Dvorak
*Assistant Examiner* — Emily Lloyd
(74) *Attorney, Agent, or Firm* — Fox Rothschild LLP; Dennis M. Carleton

(57) ABSTRACT

A device for collection of exfoliated cells from the rectal mucosa comprises a hollow, cylindrical body having an inflatable and invertible flexible membrane attached to one end thereof. Applying positive pressure to inflate the membrane after the device is inserted, preferably through a rectal access tube, into the rectum causes exfoliated cells to be collected on the surface of the membrane. Before removal of the device, negative pressure is applied and the membrane, along with the collected sample of exfoliated cells, is deflated, inverted and withdrawn into the body of the device, thereby avoiding contact of the collected sample with body surfaces or the rectal access tube as the device is removed from the rectum.

5 Claims, 6 Drawing Sheets

(56) References Cited

U.S. PATENT DOCUMENTS

| | | |
|---|---|---|
| 4,473,079 A | 9/1984 | Jasper et al. |
| 5,919,145 A | 7/1999 | Sahatjian |
| 6,171,259 B1 | 1/2001 | Fisher |
| 6,475,164 B2 | 11/2002 | Gombrich et al. |
| 6,576,429 B1 * | 6/2003 | Hallgren ........................ 435/7.1 |
| 6,921,370 B2 * | 7/2005 | Zhou et al. .................... 600/562 |

* cited by examiner

COLORECTAL CELL SAMPLING DEVICE

FIELD OF THE INVENTION

The present invention relates to a device for collecting a sample of exfoliated cells from a colorectal mucosal surface of a human subject, to a kit comprising said device and to methods of colorectal cell sampling using said device.

BACKGROUND OF THE INVENTION

Sporadic colorectal cancer (CRC) is one of the most frequently occurring and deadly of the oncological diseases affecting people in developed Western countries. It predominantly affects people over the age of 50.

A serious obstacle to early diagnosis of CRC is the absence of early, readily identifiable clinical manifestations in the majority of cases. It is only in the advanced stages of the disease, when larger tumours have formed, resulting in pain, bleeding and symptoms of obstruction, that the disease is readily diagnosed. However, the late stages of the disease are also associated with invasive or metastatic tumours. Thus, detection of colorectal tumours prior to the advanced stages of the disease would greatly increase the chances of successful surgical intervention and overall survival rates.

In the absence of early, readily identifiable clinical indications, the search for suitable CRC screening methods has continued for decades. Unfortunately, there is presently no CRC screening technique that combines low invasiveness, simplicity and low cost with high sensitivity and specificity. Two methods of screening for CRC are flexible colonoscopy/sigmoidoscopy and faecal occult blood testing (FOBT) [Rennert, G. Recent Results Cancer Res. 2003; 163: 248-253, Atkin, W. Scand. J. Gastroenterol. (Suppl.) 2003; 237: 13-16, Walsh, J. M. and Terdiman, J. P. JAMA 2003; 289: 1288-1296]. However, both of these methods have significant drawbacks.

Flexible colonoscopy/sigmoidoscopy is regarded as a precise and reliable diagnostic procedure, however, its invasiveness, cost and requirement for skilled and experienced specialists to carry out the procedure make its use in routine screening impractical. The same is true for recently introduced computed tomographic colonography (virtual colonoscopy).

FOBT is cheap and simple, however, it produces unacceptably high rates of both false negative and false positive results. Despite these limitations, FOBT is presently the screening method of choice.

Alternative methods of diagnosing CRC based upon a direct indicator of tumour presence have been investigated. One indicator that has been identified is analysis of exfoliated colonocytes. Exfoliation of colonocytes (i.e. spontaneous detachment of cells from orderly organized epithelial layer of colonic mucosa) is an important cell renewal mechanism in the human gut [Eastwood, G. L. Gastroenterology 1977; 41: 122-125]. Cytological analysis of colonocytes obtained from colonic or rectal washings (i.e. by irrigation of the colorectal mucosa) was carried out approximately 50 years ago [Bader, G. M. and Papanicolau, G. N. Cancer 1952; 5: 307-14]. This work showed that morphologically distinct exfoliated neoplastic cells could be detected in CRC patients. However, the method of obtaining these samples (an invasive colonic lavage procedure) suffered from the same disadvantages as sigmoidoscopy/colonoscopy, and required detailed cytological analysis of the sample once obtained.

The prevailing approach to obtaining samples of exfoliated epithelial cells has been to isolate them from human faeces. Human faeces were identified as a source of such cells, as the exfoliated cells of the colonic epithelium can be excreted in conjunction with other faecal matter.

The first attempts to use colonocytes isolated from human faeces for diagnostic and research purposes were started about 15 years ago by P. P. Nair and his colleagues. They claimed to be able to recover thousands of "viable" exfoliated cells from a few grams of dispersed faecal material using an isolation procedure based on density gradient centrifugation [Iyengar, V. et al., FASEB J 1991; 5: 2856-2859, Albaugh, G. P. et al., Int. J. Cancer 1992; 52: 347-350]. However, these ambitious claims have generated substantial doubts due to the low likelihood of the presence of well-preserved colonocytes in an aggressive anaerobic environment such as that found in the faeces. Furthermore, morphological evidence presented in their 1991 reference was unconvincing. P. P. Nair and members of his group maintain the validity of their approach [Nair, P. et al., J. Clin. Gastroenterol. 2003; 36(5 Suppl.) S84-S93], but have not produced any practical advances based on the outcomes of their studies.

However, despite the lack of practical advances by P.P. Nair and his colleagues, the use of human stool for diagnostic and research purposes remains an active research area as it is not associated with any invasive intervention. A number of groups have undertaken attempts to isolate colonocyte-derived genetic material (DNA) from human stool samples in order to develop diagnostic procedures employing molecular biomarkers of malignancy. Whilst DNA directly isolated from homogenized faeces can be amplified and analysed for the presence of cancer-associated genetic alterations, the absence of a highly reliable single molecular biomarker for cancer resulted in the use of multiple molecular markers reflecting a number of genetic alterations known to be present in malignant cells at relatively high frequencies. Several approaches proposing simultaneous detection of multiple mutations in the APC, K-ras and p53 genes combined with microsatellite marker analysis have been described [Ahlquist, D. A. et al., Gastroenterology 2000; 119: 1219-1227, Dong, S. M. et al., J. Natl. Cancer Inst. 2001; 93: 858-865, Rengucci, C. et al., Clin. Cancer Res. 2001; 93: 858-865, Traverso, G. et al., N. Engl. J. Med. 2002; 346: 311-320]. Methylation changes in faecal DNA have also been considered as a potential diagnostic marker [Muller, H. M. et al., Lancet 2004; 363: 1283-1285]. Although detection of colorectal tumours by multi-target molecular assays appears to be feasible, the validity of these methods for screening purposes remains questionable due to the high cost and relative complexity of laboratory procedures involved.

The search for CRC molecular markers in DNA extracted from homogenized stool samples has overshadowed the importance of the initial collection/isolation of exfoliated colonocytes. It is, however, apparent that homogenized stool is a difficult material for human DNA extraction. In particular, the abundance of bacteria in faeces can interfere with colonocyte DNA recovery procedures, and rapid mammalian DNA damage and degradation occur in the presence of anaerobic bacterial flora of the human colon.

The development of approaches based upon exfoliated colonocyte isolation has been slow partially due to a surprising lack of knowledge on cell exfoliation in the gut both in normal physiological conditions and in disease. The current views on colonocyte exfoliation are still affected by an old and unproven hypothesis implying "obligatory" exfoliation of nearly all differentiated colonocytes upon their migration to the luminal epithelium from the colonic crypts (i.e. it is presumed that there should be millions of colonocytes present in faecal matter because the cell proliferation rate of colonic epithelium is high and all cells are eventually exfoliated). It is, however, becoming clear that programmed cell death or apoptosis in situ is at least as important as exfoliation [Hall, P. A. et al., J. Cell Sci. 1994; 107: 3569-3577, Barkla, D. H. and Gibson, P. R. Pathology 1999; 31: 230-238, Ahlquist, D. A. et al., Hum. Pathol. 2000; 31: 51-57]. The relationship between these two major mechanisms of cell removal from colonic mucosa may undergo significant changes in colorectal neoplasia [Ahlquist, D. A. et al. (supra)]. Indeed, it is now proven that normal regulatory pathways leading cells to apoptosis are severely deregulated in malignant tumours [Bedi, A. et al., Cancer Res. 1995; 55: 1811-1816, LaCasse, E. C. et al., Oncogene 1998; 17: 3247-3259, Jass, J. R. Gastroenterology 2002; 123: 862-876, Oren, M. Cell Death Differ. 2003; 10: 431-442, Boedefeld, W. M. 2nd et al., Ann. Surg. Oncol. 2003; 10: 839-851] resulting in a greatly reduced apoptotic potential of cancer cells. At the same time, tumour cell adhesion is known to diminish dramatically as cancer progresses [Yamamoto, H. et al., Cancer Res. 1996; 56: 3605-3609, Haier, J. and Nicolson, G. L. Dis. Colon Rectum 2001; 44: 876-884, Leeman, M. F. et al., J. Pathol. 2003; 201: 528-534]. The latter phenomenon is important for metastatic spread, however in colorectal neoplasia, combined suppression of apoptosis and decrease in intercellular adhesion/communication greatly increases the chances of malignant cell shedding from the surface of growing tumours. If this is the case, exfoliated tumour cells, some of which can probably retain proliferative potential, should differ from their normal (non-tumour) exfoliated counterparts in: i) being more abundant due to facilitated exfoliation from the tumour surface; and ii) having much greater "survival" capacity, in particular due to higher resistance to the lack of oxygen [Graeber, T. G. et al., Nature 1996; 379: 88-91]. Upon exfoliation, these cells enter a relatively well oxygenated "mucocellular layer" that separates the colonic mucosa from the faecal contents of the gut and permanently moves distally with the flow of faeces [Ahlquist, D. A. et al. (supra)].

The importance of the mucocellular layer providing an interface between colorectal mucosa and faecal contents of the gut has not been understood until recently. Experimental studies indicated that good quality DNA could be easily obtained from the surface of rat faeces and used for further amplification and gene mutation analysis [Loktionov, A. and O'Neill, I. K. Int. J. Oncol. 1995; 6: 437-445]. These early experiments suggested that DNA extracted from colonocytes isolated from human stool surface (stool surface can be regarded as a fraction of mucocellular layer excreted with faeces) could be used for molecular analysis. A method of exfoliated cell isolation from human whole stool samples by washing cells off the surface of cooled faeces and collecting them by immunomagnetic separation procedure has been developed [Loktionov, A. et al., Clin. Cancer Res. 1998; 4: 337-342]. Although work in this direction was initially planned in terms of developing a molecular diagnostic assay for CRC, it emerged that a simple quantitative analysis of colonocyte-derived DNA from human stool surface could be used for CRC diagnosis and screening since the relative DNA amount in CRC patients was much higher compared to healthy individuals. Other authors have also reported higher amounts of either exfoliated cells [Dutta, S. K. et al., Gastroenterology 1995; 108 (Suppl.): A463] or DNA [Villa, E. et al., Gastroenterology 1996; 110: 1346-1353] in dispersed or homogenized stool samples obtained from CRC patients, however the differences between healthy people and cancer patients observed in those studies were not large enough to be considered diagnostically valid. By contrast, Loktionov et al (supra) were able to show the existence of a striking difference between CRC patients and healthy individuals employing a calculated index relating to the amount of DNA extracted from cells isolated from the stool surface to stool weight (stool DNA index or SDNAI).

The SDNAI-based diagnostic method is described in U.S. Pat. No. 6,187,546. Although the technique and results of its initial trials apparently highlighted a very efficient, simple and inexpensive approach to CRC screening, it had a number of substantial faults (apparent difficulties of whole stool handling and especially impossibility of the procedure standardization) preventing its commercialization and serious introduction into clinical practice. It has also become clear that relatively small numbers of well-preserved cells can be obtained from human stool surface using this technique [Bandaletova, et al., APMIS 2002; 110: 239-246]. These problems, difficulty of standardization being the crucial one, cause serious doubts with regard to using exfoliated colonocytes isolated from stool samples for wide scale CRC screening.

There is a good body of evidence indicating that the mucocellular layer covering human rectal mucosa is particularly rich in well-preserved exfoliated colonocytes. In addition, the cellular content of this layer in CRC patients appears to be much higher than in healthy individuals primarily due to greatly increased presence of highly resistant malignant colonocytes. Therefore CRC patients' tumour cells, which are much better adapted to autonomous existence, should quantitatively dominate the rectal exfoliated cell pool. Several recent reports describing distal (e.g. anal) implantation of persisting exfoliated cells from removed colorectal tumours [Jenner, D. C. et al., Dis. Colon Rectum 1998; 41: 1432-1434, Wind, P. et al., Dis. Colon Rectum 1998; 41: 1432-1434, Isbister, W. H. Dig. Surg. 2000; 17: 81-83, Hyman, N. and Kida, M. Dis. Colon Rectum 2003; 46: 835-836, Abbasakoor, F. et al., Ann. R. Coll. Surg. Engl. 2004; 86: 38-39] strongly corroborate this hypothesis.

Direct access to the rectal mucosa is possible by routine digital rectal examination with an examiner's gloved finger. However, although one can achieve a contact with the rectal mucocellular layer by employing this simple manipulation, significant losses of material and simultaneous contamination with irrelevant squamous epithelium of the anal canal are inevitable during the removal of the finger from the rectum. Smears prepared from gloves used for rectal examination have shown well-preserved colonocytes, combined with a high level of contamination by cells of the squamous epithelium.

There is thus a great need for direct collection of exfoliated epithelial cells from the surface of rectal mucosa without the problems of material loss and serious contamination with other tissue elements at the stage of removal of the cell-collecting surface from the rectum. Such cells could be used not only for quantitative cell and DNA analysis, but also investigated for the presence of additional cancer biomarkers (e.g. proteins) and finally assessed immunohistochemically and cytologically.

SUMMARY OF THE INVENTION

According to a first aspect of the invention, there is provided a colorectal cell sampling device comprising:
  a colorectal insertion member having a distal, insertion end, a proximal end and a closable interior cavity;
  a flexible membrane having an outer, cell sampling surface and an inner surface, wherein said membrane is sealingly attached to the distal, insertion end of said insertion member and held within the interior cavity;

such that, in use, pressurisation of the interior cavity to at least a first elevated pressure causes the membrane to emit from the distal end of said insertion member to make contact with the colorectal mucosal surface and pressurisation of the interior cavity to a second reduced pressure causes the membrane to invert and return to the interior cavity of said insertion member.

The device overcomes the difficulties with digital sampling by holding the flexible membrane within the insertion member both on insertion and withdrawal so that there is no material loss and the sample is not contaminated by cells from other surfaces (e.g. the squamous epithelium).

By sampling the mucosal surface directly, the device overcomes the difficulties associated with whole stool sampling including, the unpleasant nature of the work, the low concentration of cells obtainable, the high levels of contamination with faecal matter (especially bacteria), and especially method standardization difficulties related to such problems, for example, great variability of stool size and consistency.

Although the device is invasive, it is far less invasive than the devices currently used for colonoscopy/sigmoidoscopy, and does not require operation by a skilled and highly trained operator. The device may even be self-administered. The reduced level of invasiveness and the absence of complication risk are likely to lead to greater patient acceptance. These advantages should in turn allow for more sampling to be carried out, and at a lower cost.

In a preferred embodiment of the invention, the flexible membrane is expandable and is constructed from an elastic material. More preferably, the flexible membrane is constructed from a nitrile, latex or rubber based substance.

In a preferred embodiment of the invention, the closable interior cavity of the insertion member is closed.

In a preferred embodiment of the invention, the cell sampling device further comprises means for pressurisation of the interior cavity, wherein said means are attached to the proximal end of the insertion member.

Preferably, said means for pressurisation of the interior cavity are attached to the cell sampling device via a valve (e.g. a self-sealing valve) present at the proximal end of the insertion member.

It will be appreciated that the means for pressurisation of the interior cavity may comprise any means suitable for applying a fluid (e.g. liquid or gas) to the flexible membrane. Preferably, the means for pressurisation of the interior cavity comprise a source of compressed air, a syringe or a pump (e.g. bulb).

Preferably, the means for pressurisation of the interior cavity comprise a source of compressed air which comprises a mechanical device capable of delivering a pre-defined quantity of a first elevated pressure and a second reduced pressure to the cell sampling device. This embodiment has the advantage of accurately regulating the pressure inside the insertion member and the mechanical device has the advantage of being re-used with an indefinite number of disposable colorectal cell sampling devices.

More preferably, the means for pressurisation of the interior cavity comprise a syringe. The use of a syringe, allows for both simple operation, and for a fixed volume of air to be pumped into the flexible membrane (preferably at least a ten fold increase in the volume of air present in the flexible membrane). For example, in an embodiment of the invention where a 100 ml syringe is attached at the proximal end of the insertion member, the plunger of said syringe could initially be set at the 70-90 ml mark. A pre-defined quantity of a first elevated pressure could therefore be applied by pushing the plunger to its maximum extent (e.g. to the 0 ml mark) which would fill the flexible membrane with an air volume of 70-90 ml. A pre-defined quantity of a second reduced pressure could then subsequently be applied by pulling the plunger of the syringe back to its maximum extent (e.g. to the 100 ml mark) which would draw the membrane into the interior cavity of the insertion member. In a preferred embodiment of the invention, the syringe would be supplied with one or more retention features (e.g. snap locations) to mark the plunger positions of the syringe at each stage during use (e.g. one position prior to insertion, one during insertion and one after withdrawal). The advantage of the means for pressurisation of the interior cavity being a syringe is that the colorectal cell sampling device may be adapted to fit onto commonly available and disposable laboratory and hospital equipment.

In a preferred embodiment of the invention, the surface area of the outer, cell sampling surface of said flexible membrane is reproducibly controllable. This allows for a fixed surface area to be brought into contact with the colorectal mucosal surface being sampled, thereby providing a quantifiable collection of exfoliated cells which is correlated with the amount present on the surface of the colorectal mucosa. Preferably, the surface area is controlled by the means for pressurisation of the interior cavity. This allows for a fixed surface area to be brought into contact with the mucosal surface being sampled.

In a preferred embodiment of the invention, the insertion member is adapted to engage with a rectal access tube. This embodiment has the advantage of allowing a rectal access tube and an obturator, such as an olive shaped obturator (a conjoined rectal access tube and obturator is commonly known as a proctoscope) to be inserted first to open the rectal cavity followed by withdrawal of the obturator prior to insertion of the sampling device of the invention. The sampling device could then remain held in position with the rectal access tube for whatever period of time was required to obtain a sample. The obturator would then be replaced once the sampling device is removed and the obturator and rectal access tube would be withdrawn together.

In a preferred embodiment of the invention, the insertion member is configured to allow self-insertion. In such an embodiment, the insertion member is inserted together with a rectal access tube and therefore eliminates the need for an obturator (e.g. the insertion member has a rounded distal, insertion end). This embodiment provides the advantage that the sampling device of the invention may be self-administered, for example, patients will be easily able to sample exfoliated cells from their rectal mucosa. In this embodiment, it is envisaged that the insertion member and rectal access tube are inserted and removed together and only separated upon removal.

In a preferred embodiment of the invention, the flexible membrane forms a receptacle when held within the interior cavity of said insertion member, such that fluid may be added. This embodiment of the invention would allow for reagents to be added to the sampling device after a sample has been obtained without the need to transfer the sample to a separate receptacle, thereby losing some of the material from the sample.

In a preferred embodiment of the invention, the interior cavity of the insertion member is provided with adhesion means. This embodiment of the invention has the effect of drawing the flexible membrane towards the walls of the interior cavity of the insertion member once a sample has been obtained and application of the second reduced pressure has drawn the flexible membrane into the interior cavity of the insertion member. This feature has the advantage of providing a stable receptacle when filled with liquid.

In a preferred embodiment of the invention, the insertion member is adapted to engage with a sealing means to seal said receptacle. This would allow the sampling device, containing the sample, to be stored and transported prior to further analyses being carried out on the sample.

Preferably, the sealing means is a threaded cap. A threaded cap has the advantage of sealing the receptacle to prevent loss of sample and also allows removal for further analysis.

In the embodiment wherein the cell sampling device comprises means for pressurisation of the interior cavity, said means are preferably detachable from the insertion member. This has the advantage of converting the sampling device into a compact assay vial which may be conveniently transported and stored with many other compact assay vials for subsequent screening reactions.

In a second aspect of the invention, there is provided a kit for collecting a sample from a colorectal mucosal surface of a human subject, which comprises a colorectal cell sampling device as defined herein and a rectal access tube and optionally an obturator.

The use of a rectal access tube provides both for more comfortable insertion of the sampling device, and prevents contact between the sampling device and any surface other than the mucosal surface to be sampled. The use of an obturator in addition to the rectal access tube, may ease the discomfort of inserting the rectal access tube.

In a preferred embodiment of the invention, the kit may additionally comprise a lubricant, such as a lubricating jelly (e.g. K-Y jelly). This has the advantage of providing greater comfort during insertion of the obturator or cell sampling device of the invention.

In a preferred embodiment of the invention, the obturator is disengaged from the rectal access tube after insertion of the conjoined obturator and rectal access tube into the rectal cavity.

In a preferred embodiment of the invention, the kit further comprises sealing means, such as a threaded cap, to engage with the insertion member.

In a preferred embodiment of the invention, the kit further comprises one or more reagents, such as a buffer. The use of a buffer allows for the preparation of the sample prior to further analysis.

In a preferred embodiment of the invention, the buffer may be present in the threaded cap (e.g. as a blister packet), such that securing the cap to the insertion member releases the buffer into the receptacle (e.g. by piercing the blister packet) to suspend the cells present on the sampling surface of the flexible membrane prior to further analysis.

In a preferred embodiment of the invention, the buffer is a cell-lysis buffer which has the advantage of providing a key step prior to DNA extraction. In an alternatively preferred embodiment of the invention, the buffer is a cell-preserving medium which has the advantage of allowing enhanced cytological, biochemical and immunohistochemical analyses on the resultant cell sample. Preferably, the cell-preserving medium is supplemented with one or more cell culture components (e.g. nutrients and antibiotics).

It will be further appreciated by the person skilled in the art that any of the devices or kits previously described are suitable for sampling exfoliated epithelial tissue (e.g. colonocytes) from the surface of human colorectal mucosa.

In a third aspect of the invention there is provided a method of quantitative sampling of exfoliated cells from a colorectal mucosal surface of a human subject without contaminating the sample by contacting other body surfaces comprising the steps of:

bringing a sampling device comprising a sequestered cell sampling surface into proximity with the colorectal mucosal surface to be sampled, without making prior contact with any other body surface;

contacting the cell sampling surface with the colorectal mucosal surface such that a sample is obtained from the mucosal surface; and removing the sampling device and sample from proximity with the mucosal surface without the sequestered cell sampling surface or sample making contact with any other body surface.

This method encompasses the key steps of directly sampling exfoliated cells from a mucosal surface, and ensures that the sample is not contaminated by the cell sampling membrane making contact with other body surfaces. Contamination is avoided by sequestering the sampling surface, wherein sequestering may be defined as isolating or setting apart the sampling surface prior to bringing it into contact with the colorectal mucosal surface or after collecting cells from the colorectal mucosal surface.

In a fourth aspect of the invention there is provided a method of sampling exfoliated cells from a colorectal mucosal surface of a human subject, comprising the steps of:

inserting a colorectal cell sampling device according to the invention into the rectal cavity and bringing said device into proximity with a colorectal mucosal surface without the outer, cell sampling surface of the flexible membrane making prior contact with any other body surface;

pressurising the interior cavity to at least a first elevated pressure so that the flexible membrane emits from the distal end of the sampling device;

contacting the colorectal mucosal surface with the outer, cell sampling surface of said membrane such that a sample of exfoliated cells is obtained from the colorectal mucosal surface;

applying a second reduced pressure to the interior cavity so that the flexible membrane inverts and the sample present on the cell sampling surface of said membrane returns to the interior cavity of the cell sampling device; and removing the cell sampling device from proximity with the colorectal mucosal surface and withdrawing said device from the rectal cavity without the membrane or sample making contact with any other body surface.

It will be appreciated that the cell sampling device may additionally require a rectal access tube either alone or together with an obturator.

Thus, in a preferred embodiment of the invention, the method additionally comprises the steps of:

inserting a conjoined colorectal cell sampling device according to the invention and a rectal access tube into the rectal cavity; and removing said sampling device and sample from the rectal access tube.

In a preferred embodiment of the invention, the method additionally comprises the steps of:

inserting a conjoined rectal access tube and an obturator into the rectal cavity;

withdrawing the obturator from the rectal access tube prior to inserting a sampling device;

removing the sampling device and sample;

replacing the obturator via the rectal access tube; and withdrawing the conjoined rectal access tube and obturator from the rectal cavity.

In a fifth aspect of the invention there is provided a method of sampling exfoliated cells from a colorectal mucosal surface of a human subject, comprising the steps of:

inserting a rectal access tube and an obturator into the rectal cavity via the anal canal;
withdrawing the obturator from the rectal access tube;
inserting a colorectal cell sampling device according to the invention into the rectal cavity via the rectal access tube, without the flexible membrane of the sampling device making contact with any other body surface;
pressurising the interior cavity to at least a first elevated pressure so that the flexible membrane emits from the distal end of the sampling device;
contacting the colorectal mucosal surface with the outer, cell sampling surface of said membrane;
obtaining a sample of exfoliated cells from the colorectal mucosal surface;
applying a second reduced pressure to the interior cavity so that the flexible membrane inverts and the sample present on the cell sampling surface of said membrane returns to the interior cavity of the cell sampling device;
withdrawing the cell sampling device from the rectal cavity via the rectal access tube, without the flexible membrane of the sampling device contacting any body surface;
replacing the obturator via the rectal access tube; and
withdrawing the rectal access tube and obturator from the rectum via the anal canal.

It will be appreciated that while the rectal access tube remains inserted in the rectal cavity, a further cell sampling device of the invention may be introduced into the rectal cavity. For example, the first cell sampling device may be introduced which comprises a cell-lysis buffer to allow DNA extraction and analysis (e.g. quantitation) of any sampled cells. Thereafter, a second cell sampling device may be introduced which comprises a cell-preservation medium to allow cytological, biochemical and immunohistochemical analysis of any sampled cells.

In an alternative aspect of the invention, there is provided a sampling device for collecting a sample from a mucosal surface located within a rectal cavity of a subject, comprising:
a substantially cylindrical body, which has an open cavity at the distal end and a closable cavity at the proximal end;
a flexible membrane held within the substantially cylindrical body which forms a seal separating the open distal cavity from the closable proximal cavity; the two surfaces of the membrane being the proximal surface and the distal surface; and
means for inflation and deflation, wherein
the means for inflation can increase the internal fluid pressure of the closable proximal cavity when closed causing the membrane to evert from the distal end of the substantially cylindrical body until the distal surface of the membrane contacts the mucosal surface to be sampled; and
the means for deflation can decrease the fluid pressure of the closed proximal cavity causing the membrane to invert so that the membrane is held within the substantially cylindrical body after the distal surface of the membrane has contacted the mucosal surface to be sampled.

In a preferred embodiment of the invention, the deflation means is the valve. This embodiment of the invention would be particularly suitable for use with an elastic membrane where the internal pressure in the closable proximal cavity is greater than that outside the cavity.

In a preferred embodiment of the invention, the deflation means comprises the syringe connected to the valve.

In a second alternative aspect of the invention, there is provided a method of sampling exfoliated cells from a mucosal surface located within the rectal cavity of a human subject, comprising the steps of:
bringing a sampling device according to the invention into proximity with a mucosal surface without the sampling membrane making prior contact with any other body surface;
increasing the internal pressure of the closed proximal cavity so that the flexible membrane everts from the distal end of the sampling device;
contacting the mucosal surface with the distal surface of the membrane such that a sample of exfoliated cells is obtained from the mucosal surface;
decreasing the internal pressure of the closed proximal cavity so that the flexible membrane inverts, and it and the sample are held within the open distal cavity; and
removing the device and sample from proximity with the mucosal surface without the membrane or sample making contact with any other body surface.

In a preferred embodiment of the invention, the method comprises the steps of:
attaching a source of compressed air to the valve, and increasing the internal pressure of the closed proximal cavity by opening the valve; or
attaching a syringe to the valve and increasing the internal pressure of the closed proximal cavity by inserting the plunger.

In a preferred embodiment of the invention, the method comprises the steps of:
decreasing the internal pressure of the closed proximal cavity by opening the valve; or
decreasing the internal pressure of the closed proximal cavity by withdrawing the plunger.

In a preferred embodiment of the invention, the method comprises the steps of:
adding a cell lysis buffer or cell preserving medium to the open distal cavity of the sampling device; and
sealing the open distal cavity of the sampling device.

In a third alternative aspect of the invention, there is provided a method of sampling exfoliated cells from a mucosal surface located within the rectal cavity of a human subject, comprising the steps of:
inserting a rectal access tube and an obturator into the rectal cavity via the anal canal;
withdrawing the obturator from the rectal access tube;
inserting a sampling device according to the invention into the rectal cavity via the rectal access tube, without the flexible membrane of the sampling device making contact with any other body surface;
connecting the sampling device to a means for inflation;
increasing the internal pressure of the closed proximal cavity so that the flexible membrane everts from the distal end of the sampling device;
contacting the rectal mucosa with a fixed surface area of the sampling surface;
obtaining a sample of exfoliated cells from the surface of rectal mucosa;
decreasing the internal pressure of the closed proximal cavity so that the flexible membrane inverts, and it and the sample are held within the open distal cavity;
withdrawing the sampling device from the rectal cavity via the rectal access tube, without the flexible membrane of the sampling device contacting any body surface;
replacing the obturator via the rectal access tube;
withdrawing the rectal access tube and obturator from the rectal cavity via the anal canal;
adding a cell lysis buffer or cell preserving medium to the open distal cavity; and sealing the open distal cavity of the sampling device.

In a fourth alternative aspect of the invention, there is provided a method of screening and diagnosis for colorectal cancer which comprises any of the methods set out above and further comprising recovering the collected sample from the sampling device and performing an analysis on the sample.

In a preferred embodiment of the invention, the analysis is selected from DNA quantitation, DNA extraction followed by its quantitation and optional molecular analysis, cytological/cytochemical investigation and biochemical tests. It is to be noted that the accuracy of screening by any of these methods will be improved by the provision of a sample with low levels of contaminants and a high concentration of cells taken from the colorectal mucosal surface being sampled.

BRIEF DESCRIPTION OF THE FIGURES

The invention will now be described, by way of example only, with reference to the accompanying drawings in which.

DETAILED DESCRIPTION OF THE INVENTION

Description of Cell Sampling Embodiments

Figure 1:
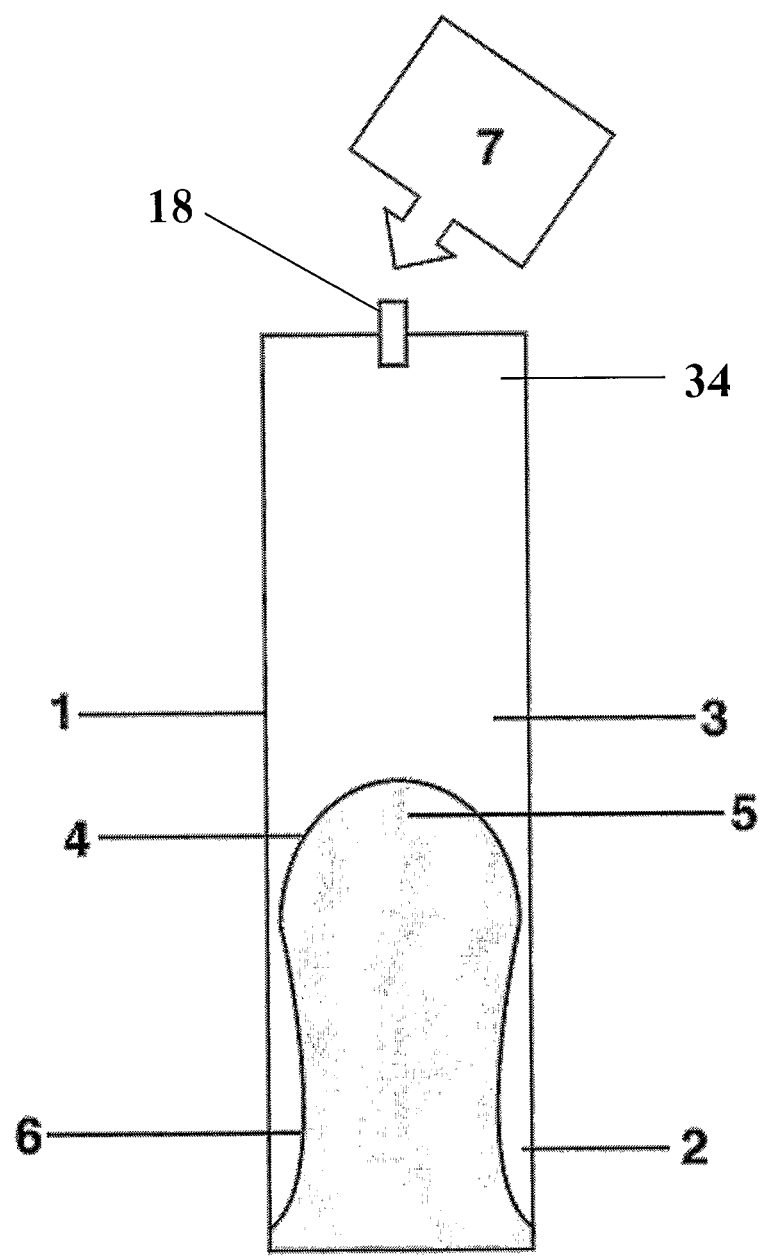
FIG. 1 shows a cross-sectional view of a cell sampling device of the invention.

The cell sampling device of FIG. 1 is designed for insertion into a rectal cavity. The device comprises a substantially cylindrical insertion member 1 with an interior cavity 3, closed at the distal insertion end 2 by a flexible and resilient membrane 4 which is sealingly attached to the member 1 at the distal end 2. In the position shown in FIG. 1, the membrane 4 is held within the cavity 3, and is adapted to emit from the cavity 3 when the cavity 3 is pressurised by means 7 (shown in more detail in FIG. 2). The membrane 4 has a cell sampling surface 5 which in the rest position shown in FIG. 1 is the inner surface, but when the membrane emits is the outer surface, and an opposing surface 6 which in the rest position is the outer surface, but which becomes the inner surface when the membrane emits. The membrane is made of nitrile, latex or a rubber based substance. At the proximal end 34, the cavity 3 is closed by a self-sealing valve 18, to which the pressurisation means 7 is adapted to be attached.

Figure 2:
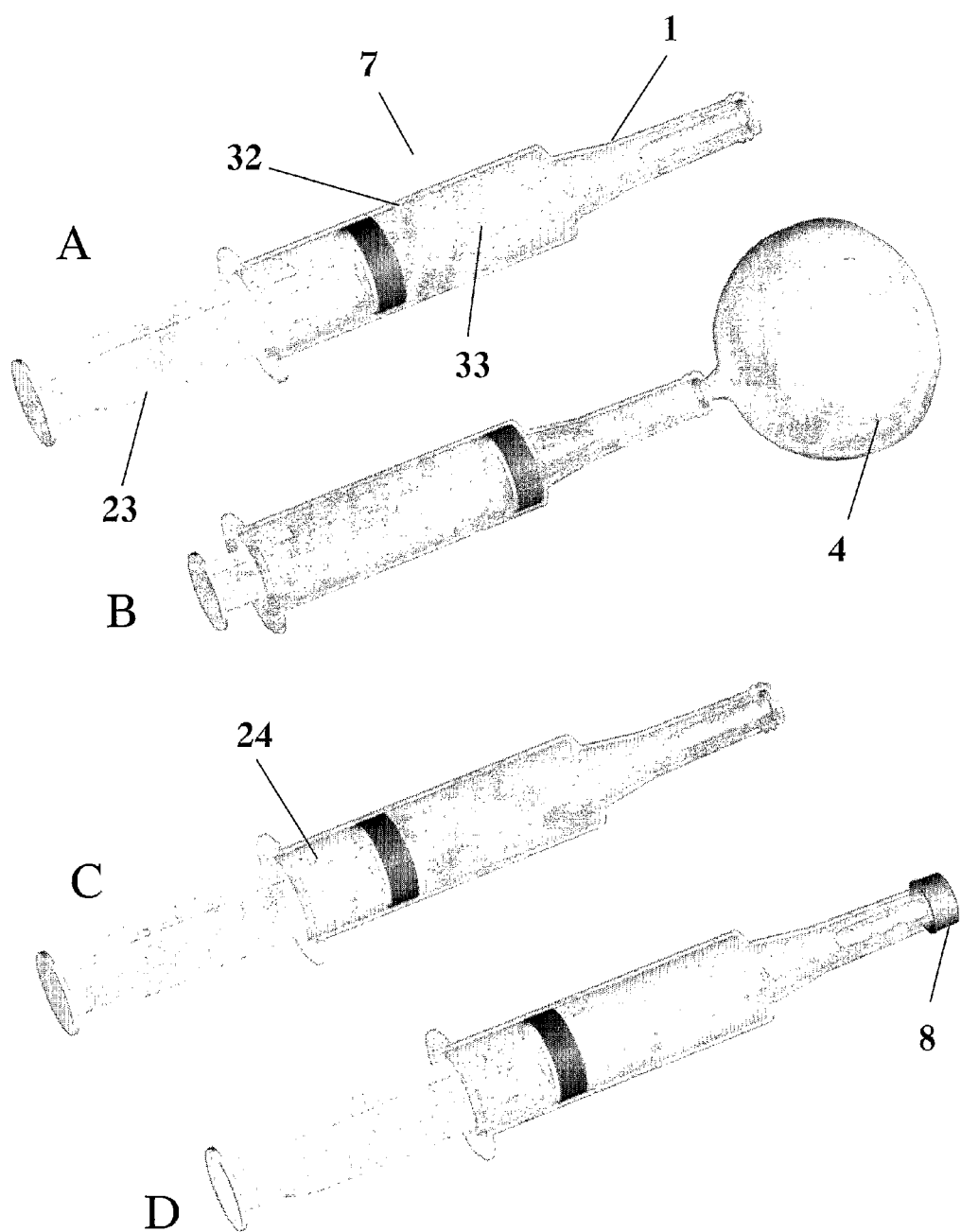
FIG. 2 shows a schematic representation of a cell sampling device of the invention wherein the means for pressurisation comprise a syringe.

The embodiment of the invention wherein the means for pressurisation of the interior cavity 7 is an integrated syringe is shown in FIG. 2 which schematically also shows the steps necessary to sample exfoliated cells from a colorectal mucosal surface of a human subject (FIGS. 2A-2D).

FIG. 2A shows a representation of the cell sampling device prior to insertion into a rectal cavity. The syringe 7 is attached to an insertion member 1 substantially as described in FIG. 1. The syringe has a plunger 23 which sealingly slides along a barrel 32 of the syringe 7 to alter the volume within an inner chamber 33 of the syringe 7. The plunger 23 of the syringe 7 is set such that 70 ml of air is present within the chamber 33 of the syringe 7.

FIG. 2B shows a representation of the cell sampling device once inserted into a rectal cavity. The plunger 23 of the syringe has been fully depressed which causes the flexible membrane 4 to inflate to a volume of 70 ml. The inflated flexible membrane 4 then makes contact with the colorectal mucosal surface of a human subject such that any exfoliated cells are transferred to the outer surface of the flexible membrane 4.

FIG. 2C shows a representation of the cell sampling device once exfoliated cells have been sampled and prior to removal from a rectal cavity. The plunger 23 of the syringe 7 is retracted such that 80 ml of air is present within the chamber of the syringe 7. This therefore creates a reduced pressure within the chamber which causes the flexible membrane 4 to be drawn back into the interior cavity of the insertion member 1 and adhere firmly to the side walls of the insertion member 1. The amount of reduced pressure may be pre-quantified by the presence of two snap fit retention features 24 (only one of which is shown in FIG. 2C). The snap fit features 24 are arms present on the plunger 23 of the syringe 7 which locate into holes on the barrel 32 of the syringe 7. The purpose of the snap fit features 24 is to prevent withdrawal of the plunger 23 from the syringe 7.

FIG. 2D shows a representation of the cell sampling device after removal from the rectal cavity and prior to cell analysis. The distal, insertion end of the insertion member 1 is provided with a thread which is adapted to receive a 20 mm diameter threaded screw cap 8. The cap 8 may have a blister packet containing a buffer such that upon screwing the cap 8 to the insertion member 1, the buffer is released into the receptacle formed by the deflated flexible membrane 4. After the cap 8 has been screwed to the insertion member 1, the syringe 7 may be detached from the insertion member 1 to allow the insertion member 1 to be converted to a compact assay vial which, along with a plurality of other vials, may be packaged and sent to a laboratory for cell analysis.

Figure 3:
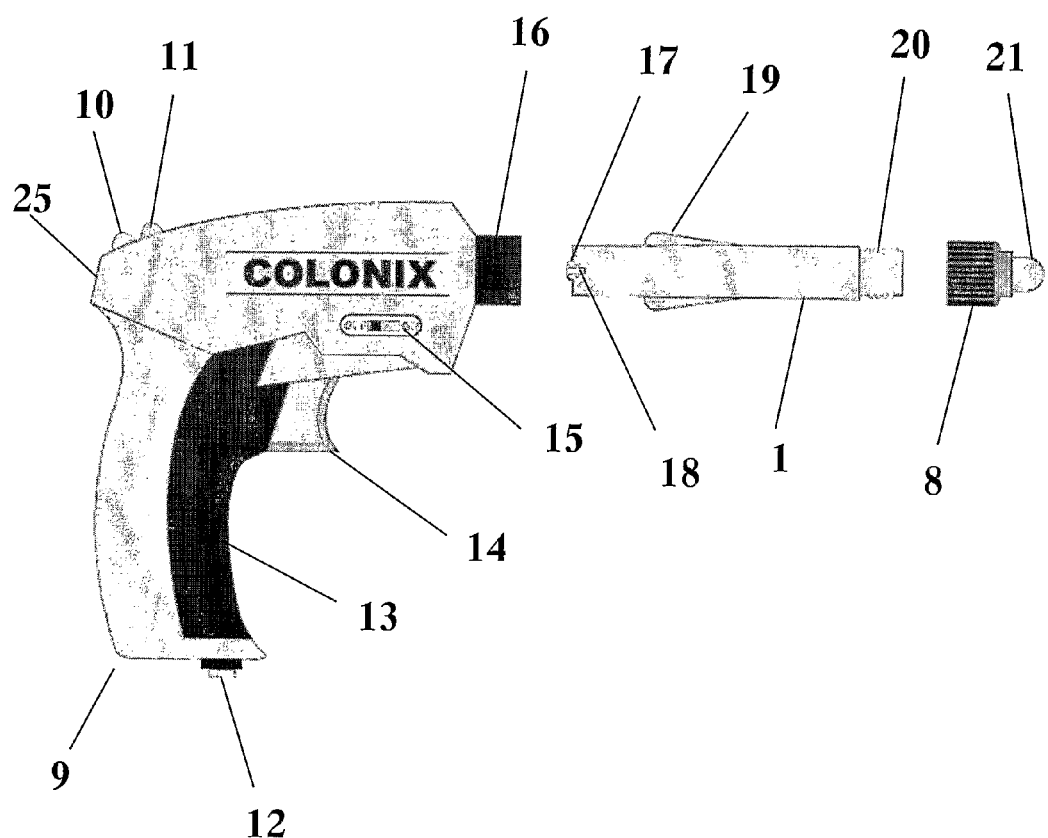
FIG. 3 shows a schematic representation of a cell sampling device of the invention wherein the means for pressurisation comprise a source of compressed air.

The embodiment of the invention wherein the means for pressurisation of the interior cavity 7 is a source of compressed air is shown in FIG. 3. This figure schematically shows a mechanical device 9 which is a pump operated by an electrical motor (not shown) capable of delivering repeated doses of a first elevated pressure followed by a second reduced pressure upon activation of the trigger 14. The mechanical device 9 is capable of attachment to an insertion member 1 substantially as described in FIGS. 1 and 2 by way of a click-fit locator 16 present on the mechanical device 9 which co-operates with a locating lug 17 on the insertion member 1. A self-sealing valve 18 is present on the insertion member 1 to ensure pressure is maintained within the insertion member 1 upon disconnection from the mechanical device 9. The insertion member 1 comprises vanes 19 which are designed to engage with a proctoscope and is threaded 20 at the distal insertion end in order to receive a threaded cap 8 having a blister packet 21 containing buffer. The mechanical device 9 is intended to be battery powered and may be recharged by a power supply through a charging jack 12. The mechanical device 9 comprises an air intake filter 25, a rubberised handle 13 and also has an on-off switch 15 and light emitting diodes 10 and 11 which indicate when the device 9 is ready and when the cycle of first and second pressure applications are complete.

In use, a user holds the mechanical device 9 by the rubberised pistol type handle grip 13 and attaches the device 9 to an insertion member 1. The insertion member is then inserted into the rectal cavity where it engages with a proctoscope using the vanes 19 which enables an improved penetration consistency. A first elevated pressure is applied by the user by pressing the trigger 14 which causes air to be drawn into the mechanical device 9 through the air intake filter 25 which is then compressed and causes the flexible membrane to emit from the distal end of the insertion member 1 to make contact with the colorectal mucosal surface. A second reduced pressure is then applied by the user by pressing the trigger 14 a second time which causes the flexible membrane to return to the interior cavity of the insertion member 1. Once cell sampling has been completed, the insertion member 1 is disengaged from the proctoscope and the mechanical device 9 is detached from the insertion member 1 and the pressure within the insertion member 1 is maintained by way of the self-sealing valve 18. A threaded cap 8 having a buffer containing blister packet 21 may then be screwed to a thread 20 on the insertion member 1 causing buffer to be released into the receptacle formed by the deflated flexible membrane. The mechanical device 9 can then be re-used by attachment to subsequent insertion members 1.

Components Required for the Touch-Print Cell Sampling Technique

Figure 4:
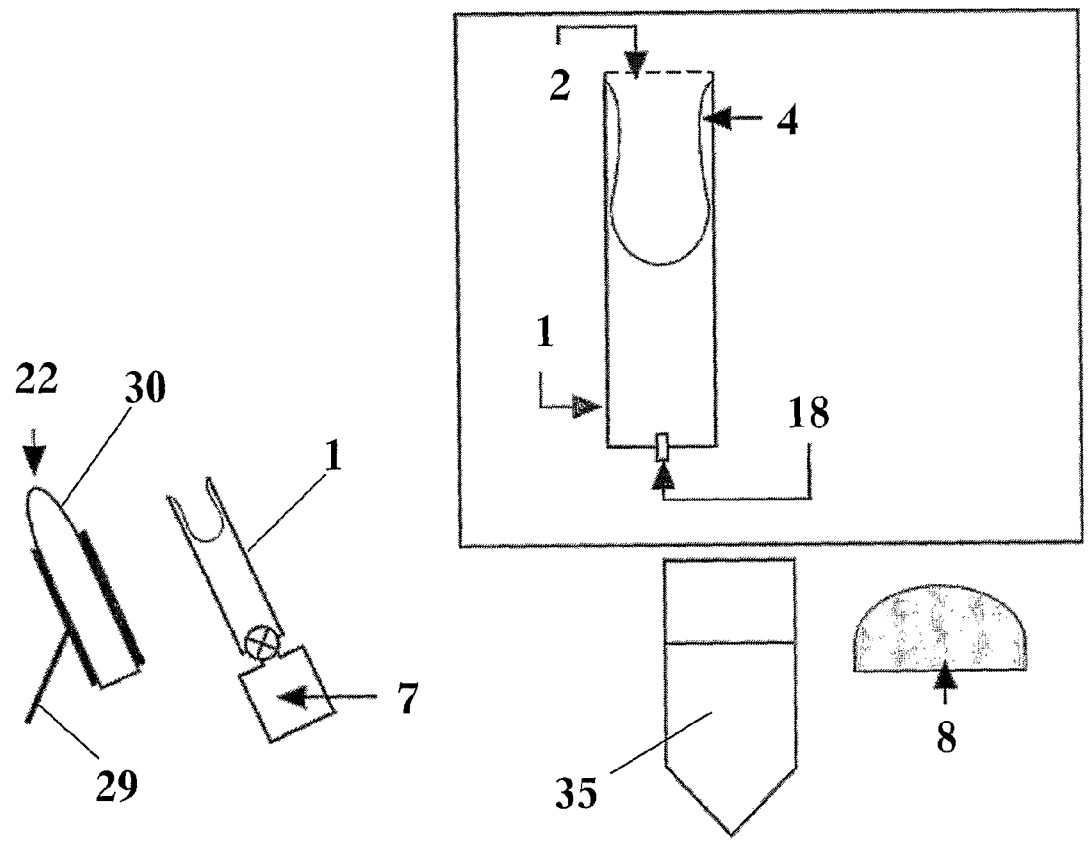
FIG. 4 shows the components required for sampling exfoliated cells from a colorectal mucosal surface of a human subject.

The components required for sampling exfoliated cells from a colorectal mucosal surface of a human subject are presented in FIG. 4.

i) Access to the rectal mucosa can be achieved by the use of a rectal access tube 29, which can be a modification of an existing instrument for rectal examination (e.g. rectoscope 22). The rectal access tube 29 consists of a rigid tube (with a handle) equipped with an obturator 30 providing an olive-shaped end and uninterrupted surface facilitating introduction of the rectal access tube 29 through the anal canal into the rectum.

ii) The cell sampling device 1 shown in FIG. 4 is substantially as described in FIG. 1 and has an external diameter compatible with the internal diameter of the rectal access tube, i.e. in the range of 15-20 mm.

iii) A source of compressed air 7 serves to provide a means for pressurisation of the interior cavity. The means for pressurisation 7 may comprise a syringe (as described in FIG. 2), an air pump (as described in FIG. 3) or a compressed air mini-container (mini-cylinder). Air pressure inside the cell-sampling device can be limited/controlled by either using a fixed air volume (simple syringe solution) or by reaching a fixed air pressure level (a precision valve would be needed for this purpose).

iv) A bottle or tube with a specific buffer 35 (different buffers should be used for different purposes, such as DNA or RNA extraction or cell isolation/separation for further analysis).

v) A hermetic lid 8 for the cell-sampling device (needed for cell/protein lysis reactions if immediate DNA or RNA extraction is performed, for cell isolation procedures and, especially, for storage/transportation of the material if it is not immediately used, e.g. transportation from surgery/clinic to laboratory).

The components required for the procedure can be developed to be used as a disposable kit, which should include all the listed components except the compressed air source, which can be used repeatedly.

Description of the Touch-Print Cell Sampling Technique (Rectal Manipulations)

Figure 5:
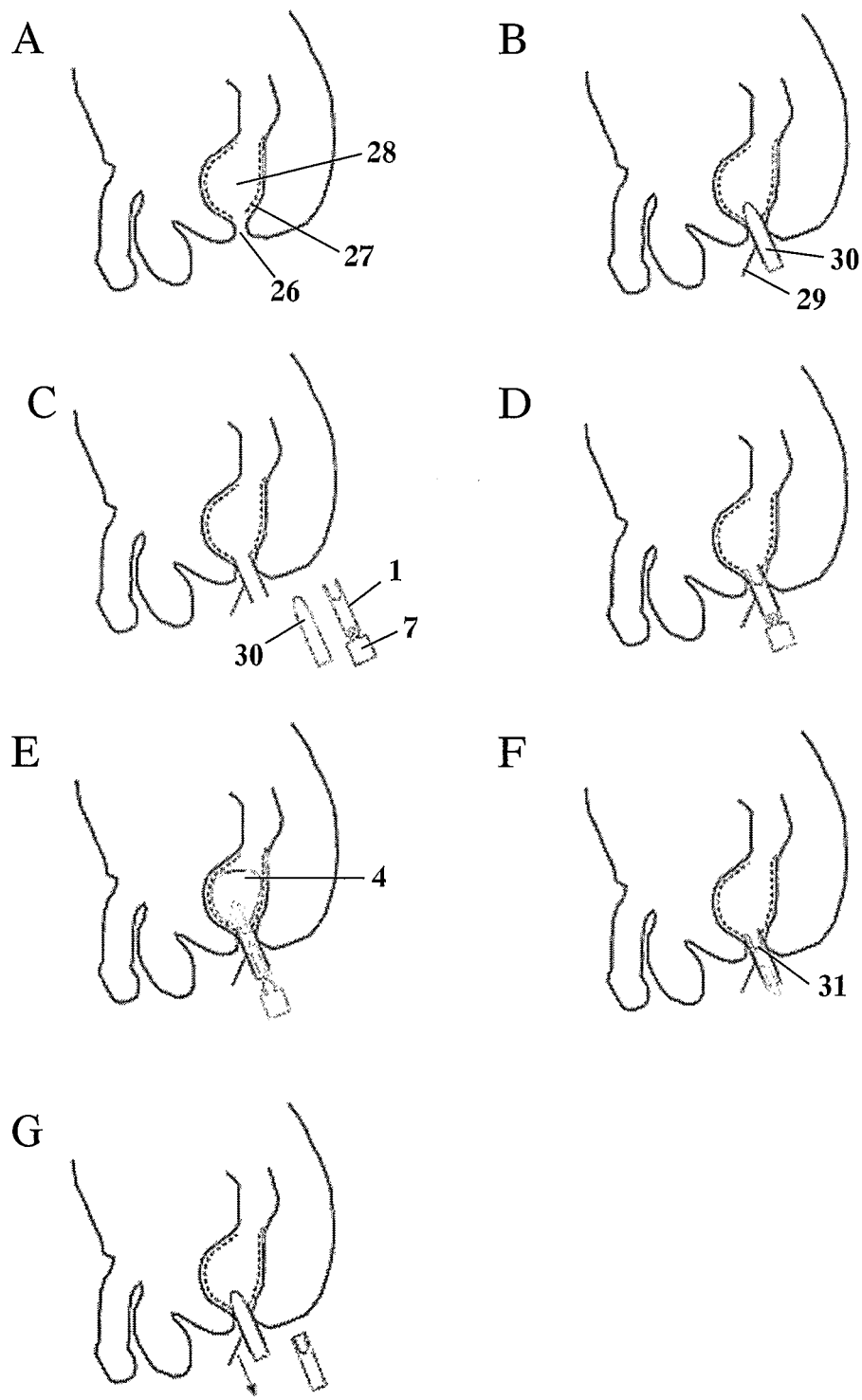
FIG. 5 shows an example of a method of sampling exfoliated cells from a colorectal mucosal surface of a human subject using any of the devices shown in FIGS. 1-4.

FIG. 5 shows an example of the touch-print cell sampling technique to sample exfoliated cells from a colorectal mucosal surface of a human subject using any of the devices shown in FIGS. 1-4. This procedure is simple and no special training in proctology or endoscopy is required for the operator to carry it out. It can be performed by any qualified medical professional (GP, nurse etc.) at a local surgery or patient's home or it may even be self-administered by the patient.

FIG. 5A schematically illustrates a cross-section of the anatomy of the human rectum 28, anal canal 26 and colorectal mucocellular layer 27. It should be noted that any contact of the cell-sampling device with squamous epithelium of anal canal can result in both material loss and contamination of the sample with squamous epithelium of the anal canal.

The procedure commences with introduction of a rectoscope-like rectal access tube 29 with an obturator 30 in place into the rectum 28 (FIG. 5B). An appropriate lubricant can be used for the introduction procedure to facilitate it and to diminish patient's discomfort, which can be caused by this initial stage of the procedure.

Once the rectal access tube 29 is introduced (FIG. 5C) and the obturator 30 has been removed, direct access to rectal mucosa is achieved and the mucocellular layer 27 opens.

The insertion member 1 is introduced to the rectal access tube 29 so that the upper edge of the insertion member is located just above the edge of the rectal access tube (FIG. 5D).

A first elevated pressure is applied which inflates the collecting flexible membrane in order to contact the membrane with the rectal mucocellular layer 27 to provide touch-print cell sampling (FIG. 5E). The device is left in this position for approximately 10-15 seconds to achieve better adhesion of exfoliated cells and cell-derived materials of the mucocellular layer to the collecting membrane.

FIG. 5F shows the application of a second reduced pressure which deflates the flexible membrane and causes it to return to its initial position with collected material 31 on the outer, cell sampling surface.

The insertion member 1 is removed from the rectal access tube 29 and taken for further manipulations and analyses. The obturator 30 (a new re-lubricated one can be used) is reinstalled into the rectal access tube 29, and the tube 29 is removed from the rectum 28 (see FIG. 5G). The complete procedure (rectal manipulations) should take no more than a couple of minutes.

Processing of Collected Cells.

Figure 6:
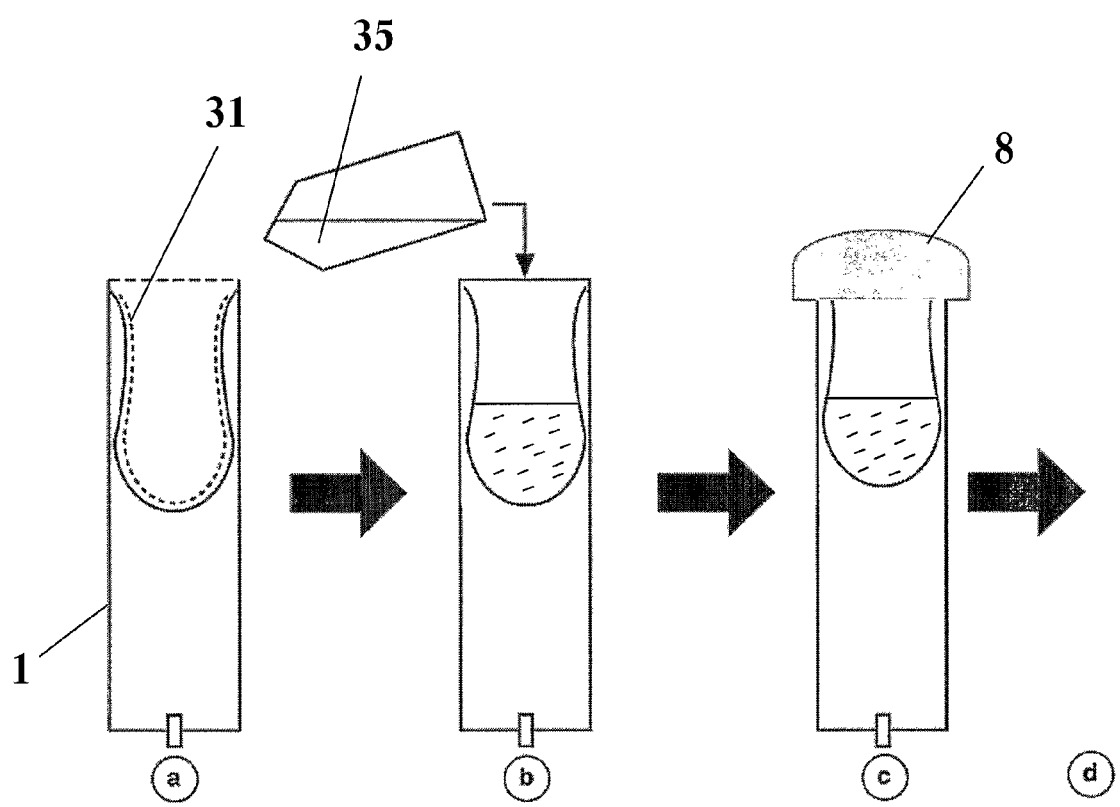
FIG. 6 shows an example of the steps which may follow the method depicted in FIG. 5.

FIG. 6 shows an example of the steps which may follow the method depicted above for FIGS. 5A-5G which should be completed immediately after cell collection to avoid drying of the cell collection membrane. Step (a) shows cell-sampling device 1 with exfoliated cells 31 on the cell-collecting flexible membrane after cell collection. The top compartment of the cell-sampling device is filled with a fixed volume of a specific buffer 35 which lyses or suspends the exfoliated cells (Step (b)). Different cell lysis buffers or cell preserving mediums can be used for DNA or RNA extraction procedures, special buffers/mediums should be used for applications requiring cell isolation. The cell-sampling device is prepared for sample transport or storage by being hermetically closed with a secure threaded cap 8 (step (c)) but it will be appreciated that when the threaded cap has a buffer containing blister packet then step (b) can be omitted. The device can then be stored or transported for further downstream procedures for screening/diagnostic and/or research purposes (step (d)).

Analysis of Samples

It should be stressed that the technique provides a much higher degree of standardization in comparison with other existing approaches. The use of a standard device with standard air pressure/volume, standard area of inflated collection membrane (contact area with rectal mucocellular layer can vary, but this variation is negligible compared to other ways of obtaining exfoliated cells, e.g. stool-based techniques) and standard amount of buffer added after the cell sampling procedure create very favourable conditions for comparative analysis of either cell numbers or amounts of cell-derived substances (e.g. DNA).

(a) Analysis of Samples for the Purpose of Colorectal Cancer Screening

Colorectal cancer screening implies wide, population-based (age-defined) assessment of individuals presenting no complaints to reveal asymptomatic (in most instances—early) cases of the disease, timely treatment of which can reduce mortality caused by the condition. One necessary requirement for the method is its simultaneous applicability for thousands/millions of people.

i) Given that there are strong indications of considerably higher amounts of colonocytes and colonocyte-derived DNA in rectal mucocellular layer of colorectal cancer patients compared to tumour-free individuals, it is very likely that the technique of direct sampling of exfoliated colonocytes and colonocyte-derived materials can provide a simple screening test for colorectal cancer based on the direct quantitation of the amount of DNA extracted from the cells. For this approach the initial buffer used just after cell sampling should be a cell lysis buffer used for the selected DNA extraction procedure. The addition of the buffer should provide efficient cell lysis and preservation of the DNA-containing material during transportation to a dedicated laboratory and (probably) some period of storage. The DNA extraction method should be selected on the basis of its applicability for high throughput analysis, i.e. it should be compatible with multi-channel liquid handling robotic systems. Exact values for DNA quantities defining "positive", "negative" and "doubtful" results of the test should be determined in clinical trials.

ii) Similar initial steps of DNA extraction can be applied for the analysis of molecular markers of colorectal cancer. Cells sampled by the touch-print procedure should provide a much better quality DNA compared to currently employed techniques of DNA extraction from stool samples. PCR amplification of this DNA can be done without precise quantitation of its amount. Multi-target molecular analysis is considered as an option in colorectal cancer screening, however it may be more time-consuming and expensive compared to direct quantitative analysis. At the same time DNA extracted for direct quantitation can certainly be used for PCR amplification in further diagnostic analysis of quantitatively "positive" or "doubtful" cases.

iii) In case of a need for specific isolation of colonocytes from cells of other types, separation methods (e.g. immunomagnetic or density gradient separation) can be applied to achieve a higher purity of colonocyte cell population for the analysis. For this purpose some cell-preserving media containing antibiotics (some bacterial presence in the collected material is impossible to avoid) and mucolytic agents can be applied. Isolated colonocytes can then be used for different types of analysis such as DNA extraction and quantitation, DNA extraction followed by PCR amplification, cancer molecular and biochemical marker analysis, cytological/cytochemical assessment, and direct cell counting (doubtful in terms of screening due to low speed and high cost).

(b) Colorectal Cancer Diagnosis

Diagnostic use of tests is focused on individuals presenting some specific complaints or already identified as sufferers from a condition. Target groups of patients are much smaller than those expected for screening purposes.

i) Direct DNA quantitation can be applied in individuals presenting complaints indicating possible colorectal conditions.

ii) DNA extraction followed by PCR amplification and molecular analysis can be useful both for confirmation of the initial diagnosis and for advanced diagnostic procedures (assessment of cancer aggressiveness, sensitivity to chemotherapy for metastatic tumours, prognosis etc.).

iii) Cell isolation can be used for both further molecular/biochemical analysis and cytological investigation (tumour cells with specific morphological features) can be easily found among exfoliated colonocytes in CRC patients.

The invention claimed is:

1. A method of sampling exfoliated cells from a colorectal mucosal surface of a human subject, comprising the steps of:
   providing a colorectal sampling device comprising:
      a colorectal insertion member having a distal, insertion end, a proximal end and an interior cavity;
      a flexible membrane having an outer, cell sampling surface and an inner surface, wherein said membrane is sealingly attached to the distal, insertion end of said insertion member and, when held within the interior cavity, forming a receptacle having said cell sampling surface on the interior thereof, said receptacle being open to said insertion end of said insertion member;
      threads, defined at the tip of said insertion end of said insertion member; and
      a threaded cap, which, when engaged with said threads defined at the tip of said insertion end, seal said insertion end to form a closed cavity, said closed cavity defined by said cell sampling surface of said flexible membrane and said threaded cap;
   inserting the colorectal insertion member into the rectal cavity and bringing said insertion member into proximity with a colorectal mucosal surface without the outer, cell sampling surface of the flexible membrane making prior contact with any other body surface;
   pressurizing the interior cavity to at least a first elevated pressure so that the flexible membrane emits from the distal end of the insertion member;
   contacting the colorectal mucosal surface with the outer, cell sampling surface of said membrane such that a sample of exfoliated cells is obtained from the colorectal mucosal surface;
   applying a second reduced pressure to the interior cavity so that the flexible membrane inverts and the sample present on the cell sampling surface of said membrane returns to the interior cavity of the insertion member, said flexible membrane forming said receptacle with said cell sampling surface, and said sample on the interior of said receptacle;
   removing the insertion member from proximity with the colorectal mucosal surface and withdrawing said insertion member from the rectal cavity without said flexible membrane or sample making contact with any other body surface;
   adding a liquid buffer to said receptacle formed by said cell sampling surface of said flexible membrane; and
   sealing said receptacle by engaging said threaded cap with said threads defined at the tip of said insertion end of said insertion member, said closed cavity containing said sample.

2. A method as defined in claim 1, wherein the step of inserting the colorectal insertion member into the rectal cavity further comprises inserting the colorectal insertion member while conjoined with a rectal access tube; and further comprising the step of:
removing said insertion member and sample from the rectal access tube.

3. A method as defined in claim 1, wherein the step of inserting the colorectal insertion member into the rectal cavity further comprises inserting the colorectal insertion member through a rectal access tube; and further comprising the steps of:
joining the rectal access tube and an obturator;
inserting the conjoined rectal access tube and obturator into the rectal cavity;
withdrawing the obturator from the rectal access tube;
removing the insertion member and sample from the rectal access tube;
replacing the obturator via the rectal access tube; and
withdrawing the conjoined rectal access tube and obturator from the rectal cavity.

4. A method as defined in claim 1, further comprising the step of recovering the collected sample from the sampling device and performing a diagnostic analysis on the sample.

5. A method as defined in claim 1, and further comprising the step of transporting and storing the collected sample in said colorectal sampling device.

* * * * *